United States Patent [19]

Buzas et al.

[11] 4,051,259
[45] Sept. 27, 1977

[54] PHENOXYACETIC ACID AMIDE

[75] Inventors: André Buzas, Bievres; Jacques Bruneau, Neuilly-sur-Seine, both of France

[73] Assignee: Les Laboratoires Bruneau & Cie, France

[21] Appl. No.: 672,967

[22] Filed: Apr. 2, 1976

[30] Foreign Application Priority Data

Apr. 8, 1975 France .................. 75.10890

[51] Int. Cl.² .................. A61K 31/165; C07C 103/75
[52] U.S. Cl. .................. 424/324; 260/559 A
[58] Field of Search .................. 260/559 A; 424/324

[56] References Cited

U.S. PATENT DOCUMENTS 3,843,647 10/1974 Buzas .................. 424/324 X

Primary Examiner—Frederick E. Waddell
Attorney, Agent, or Firm—Stevens, Davis, Miller & Mosher

[57] ABSTRACT

The invention relates to 1-methyl-2-(m-trifluoromethyl-phenyl)-ethylamide of p-pentylaminophenoxyacetic acid and its pharmaceutically acceptable acid addition salts which have outstanding anorexigenic properties.

3 Claims, No Drawings

PHENOXYACETIC ACID AMIDE

The present invention relates to 1-methyl-2-(m-trifluoromethylphenyl)-ethylamide of p-pentylaminophenoxyacetic acid, its pharmaceutically acceptable acid addition salts and pharmaceutical compositions containing them.

In U.S. Pat. No. 3,843,647 of the applicant there are described phenoxyacetic acid derivatives of the formula:

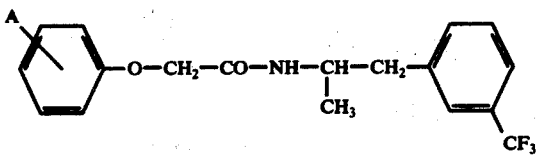

in which A can be in the ortho, meta or para position and is $NH_2$, RCONH, $NHR_1$, $NR_2R_3$ or $NHCONR_4R_5$, R is hydrogen or a linear or branched, saturated or unsaturated, aliphatic hydrocarbyl radical; each of $R_1$, $R_2$ and $R_3$ is an alkyl radical; and each of $R_4$ and $R_5$ is hydrogen, an alkyl radical, or an aminoalkyl radical in which the amino group may be derived from a heterocyclic amine. These compounds display pharmacological activities, especially as agents which cause anorexia and in some cases also dispel anxiety and/or counteract inflammation. In claim 1 of the aforesaid specification there are claimed inter alia those compounds of the aforementioned formula wherein A is in the para-position and represents a grouping $(C_{1-3}alkyl)NH$.

It has now been found as a result of further research and experimentation of those phenoxyacetic acid derivatives of general formula I wherein A represents a grouping —$NHR_1$ wherein $R_1$ = alkyl, that the $R_1$ = n-pentyl derivative, which is hitherto an unknown compound, possesses outstanding anorexia-inducing properties and low toxicity.

The present invention therefore provides a phenoxyacetic acid derivative of the general formula:

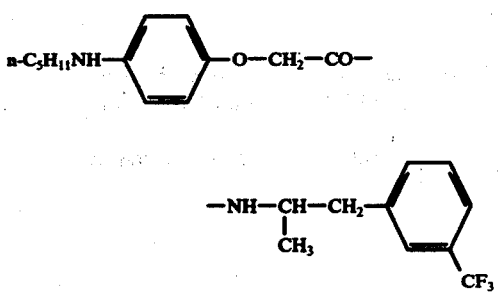

and pharmaceutically acceptable organic or inorganic acid addition salts thereof, e.g. hydrochlorides.

The compound of the invention may be prepared by the process which comprises the reduction of a corresponding amide derivative of the general formula:

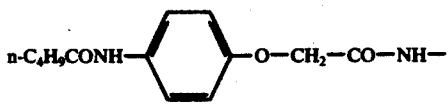

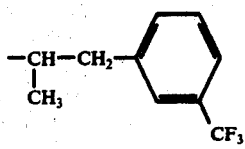

(which may be obtained by butyrylation of the corresponding amino derivative described in example 1 of U.S. Pat. No. 3,843,647) by means of a hydride, such as lithium aluminium hydride, in an inert organic solvent such as diethyl ether or tetrahydrofuran or another ether, preferably of higher boiling point.

The phenoxyacetic acid derivative (II) may also be prepared by the reduction, by means of sodium borohydride or by catalytic hydrogenation, of the compound obtained by direct condensation of the amino-derivative described in example 1 of U.S. Pat. No. 3,843,647 of the formula:

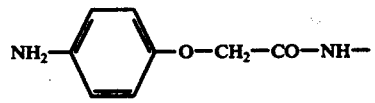

and n-pentanal.

The phenoxyacetic acid derivative (II) may also be prepared by the process which comprises the reaction of a halogeno compound of the formula:

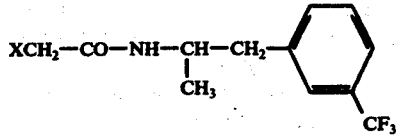

(wherein X represents a halogen atom) with p-n-pentylaminophenol, in an alcohol in the presence of a base which can be the alkoxide corresponding to the alcohol employed, for example sodium ethoxide and ethyl alcohol.

The following example illustrate the preparation of phenoxyacetic acid derivative of the present invention.

EXAMPLE

1-Methyl-2-(m-trifluoromethylphenyl)-ethylamide of p-pentylaminophenoxyacetic acid and its hydrochloride 14.1 g (0.04 mol) of 1-methyl-2-(m-trifluoromethylphenyl)-ethylamide of p-aminophenoxyacetic acid and 4 g of pentanal are mixed in a small reactor. When the evolution of heat ceases, 30 ml of methanol are added and 3 g of sodium borohydride are added in small portions whilst cooling. The mixture is stirred for 3 hours at ambient temperature. The methanol is driven off. The residue is taken up in 100 ml of 1N hydrochloric acid. The solution is washed once with benzene and is rendered alkaline with sodium carbonate, and the base is then extracted with benzene. The benzene is driven off to give 15 g of 1-methyl-2-(m-trifluoromethylphenyl)- ethylamide of p-pentylaminophenoxyacetic acid; yield 85%. IR Spectrum: NH bands at 3,400 and 3,300 cm$^{-1}$; CO band at 1,660 cm$^{-1}$.

The hydrochloride of the base is prepared directly in ethyl alcohol by adding the requisite amount of 4N hydrochloric acid. The mixture is evaporated to dryness and the residue is triturated with diethyl ether to give beautiful white crystals. They are recrystallised from ethyl acetate; melting point 160° C.

The compounds of formula (I) wherein A represents a p-alkylamino group were subjected to pharmacological investigation.

The toxicity (LD50) has been determined in the mice by the method of Karber and Behrens (Arch. Expl. Pathol. Pharmacol., 1931, 162, 48) and the anorexigenic activity (ED50) in the rat by the method of LeDouarec (J. Pharmacol. Paris 1970, 1, 419–22). The results obtained are listed in the following table.

TABLE

| Code N° | R$_1$ | LD$_{50}$ po | ED$_{50}$ po (anorexia) |
|---|---|---|---|
| LB 367 | methyl | 800 mg/kg | 12 mg/kg |
| LB 359 | ethyl | 1 600 mg/kg | 15 mg/kg |
| LB 368 | n-propyl | > 1 600 mg/kg | 20 mg/kg |
| LB 448 | n-butyl | > 2 000 mg/kg | 20 mg/kg |
| LB 369 | isobutyl | > 2 000 mg/kg | 25 mg/kg |
| LB 411 | n-pentyl | 4 000 mg/kg | 10 mg/kg |
| LB 446 | n-hexyl | > 4 000 mg/kg | 45 mg/kg |

When comparing these results one may see that the anorexigenic activity and the toxicity decrease in the same time from methyl to butyl.

However the activity of the pentyl compound is particularly high while its toxicity is very low. Moreover it was stated that the intoxication symptoms appear only at doses near of the LD50 and are yet relatively weak: hypomotility and hypothermia during the first hour than tremor and convulsions.

The compound of the present invention can be used in human medicine and in veterinary medicine as an anorexia-inducing agent.

The invention includes within its scope pharmaceutical compositions comprising, in association with a pharmaceutical carrier, the compound of formula II (LB411) or a pharmaceutically acceptable acid addition salt thereof.

The compound is especially suitable for oral administration, e.g. in the form of pills or capsules, and the daily dose is preferably 50 to 250 mg. The pills or capsules may contain for example 50 to 100 mg of active principle:

| capsule | : LB411 | 0,05 g |
| | lactose | 0,10 g |
| pill | : LB411 | 0,100 g |
| | microcristalline cellulose | 0,020 g |
| | starch | 0,020 g |
| | carboxymethylated starch | 0,001 g |
| | gum-acacia | 0,001 g |
| | magnesium-stearate | 0,0015 g |
| | magnesium-silicate | q.s. 0,200 g |

What we claim is:

1. Phenoxyacetic acid derivative of the formula:

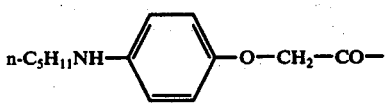

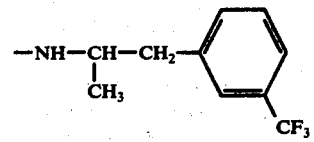

II and its pharmaceutically acceptable acid addition salts.

2. A method of inducing anorexia in man which comprises orally administering a compound of the formula

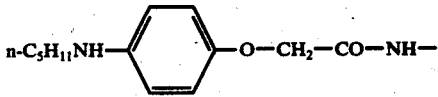

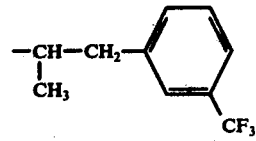

or a pharmaceutically acceptable acid addition salt thereof to a patient in an amount sufficient to induce anorexia.

3. A method of claim 2, wherein said amount is 50 to 250 mg per day.